(12) United States Patent
Kleber et al.

(10) Patent No.: US 8,875,564 B2
(45) Date of Patent: Nov. 4, 2014

(54) METHOD AND DEVICE FOR DETECTING CONTAMINANTS IN A FLUID

(75) Inventors: Jörg Kleber, Neunkirchen (DE); Sascha Gross, Püttlingen (DE); Horst Mannebach, Münstermaifeld (DE); Arnt Kohlrausch, Kreuztal (DE); Wolfgang Igelhorst, Mülheim a.d. Ruhr (DE)

(73) Assignees: Hydac Filter Systems GmbH, Sulzbach/Saar (DE); SMS Siemag Aktiengesellschaft, Düsseldorf (DE)

( * ) Notice: Subject to any disclaimer, the term of this patent is extended or adjusted under 35 U.S.C. 154(b) by 226 days.

(21) Appl. No.: 13/322,979

(22) PCT Filed: Jun. 4, 2010

(86) PCT No.: PCT/EP2010/003389
§ 371 (c)(1),
(2), (4) Date: Dec. 27, 2011

(87) PCT Pub. No.: WO2010/142403
PCT Pub. Date: Dec. 16, 2010

(65) Prior Publication Data
US 2012/0103091 A1    May 3, 2012

(30) Foreign Application Priority Data
Jun. 8, 2009    (DE) .......................... 10 2009 024 561

(51) Int. Cl.
*G01N 33/00*    (2006.01)
*G01N 33/28*    (2006.01)
*G01N 15/06*    (2006.01)
*G01N 1/38*    (2006.01)

(52) U.S. Cl.
CPC .......... *G01N 1/38* (2013.01); *G01N 2015/0693* (2013.01); *G01N 33/2888* (2013.01); *G01N 2001/383* (2013.01); *G01N 15/06* (2013.01)

USPC ....................................... 73/61.41

(58) Field of Classification Search
CPC ......... G01N 1/38; G01N 15/02; G01N 15/06; G01N 2001/383; G01N 2015/0283; G01N 33/2858; G01N 15/0205; G01N 15/10; G01N 33/30
USPC ............ 73/53.05, 53.07, 61.41, 61.42, 61.71, 73/863.01, 864.81, 865.5; 356/335, 336
See application file for complete search history.

(56) References Cited

U.S. PATENT DOCUMENTS 3,902,115 A * 8/1975 Hogg et al. .................. 324/71.1
4,095,472 A * 6/1978 Mowery, Jr. ................. 73/61.56
(Continued)

FOREIGN PATENT DOCUMENTS

DE    10060609        9/2002
DE    102006005956    8/2007
(Continued)

OTHER PUBLICATIONS

Vertrag Über Die Internationale Zusammenarbeit Auf Dem Gebiet Des Patentwesens, Form PCT/ISA/220, Jul. 2009, 15 pages.
(Continued)

*Primary Examiner* — Randy W Gibson
*Assistant Examiner* — Natalie Huls
(74) *Attorney, Agent, or Firm* — Roylance, Abrams, Berdo & Goodman LLP

(57) ABSTRACT

A method and a device detects contaminants in a fluid (1). Fluid (2) with particles is conveyed by a first metering pump (3) to a device (4) for measuring the contamination or the particle density in the contaminated fluid (2). Before entering the device (4) for measuring the contamination, the fluid is mixed with cleaned fluid (5) in a defined mixing ratio. The particle density or the contamination of the mixed fluid (6) is measured. The particle density or the contamination of the contaminated fluid (2) is determined by an arithmetic unit (7).

16 Claims, 5 Drawing Sheets

(56) References Cited

U.S. PATENT DOCUMENTS

| | | | |
|---|---|---|---|
| 4,583,396 A | | 4/1986 | Hunt et al. |
| 4,794,806 A | * | 1/1989 | Nicoli et al. ............... 73/863.01 |
| 5,007,297 A | * | 4/1991 | Sommer ....................... 73/865.5 |
| 5,332,512 A | | 7/1994 | Wells |
| 5,586,161 A | | 12/1996 | Russell et al. |
| 5,739,916 A | | 4/1998 | Englehaupt |
| 6,007,235 A | | 12/1999 | Freud et al. |
| 6,211,956 B1 | | 4/2001 | Nicoli |
| 6,582,661 B1 | * | 6/2003 | Pardue et al. ................. 422/68.1 |
| 6,947,126 B2 | * | 9/2005 | Grant et al. ..................... 356/36 |
| 7,002,684 B2 | * | 2/2006 | Ikeda et al. ................... 356/336 |

FOREIGN PATENT DOCUMENTS

| | | |
|---|---|---|
| DE | 10110156 | 1/2009 |
| DE | 202008013327 | 3/2009 |
| EP | 0290397 | 11/1988 |
| FR | 2448746 | 9/1980 |
| JP | 62255849 A | 11/1987 |
| JP | 2002039935 A | 2/2002 |
| WO | 2007/145529 | 12/2007 |

OTHER PUBLICATIONS

Deutsches Patent—und Markenamt, München, Germany, May 20, 2010, 3 pages.

* cited by examiner

METHOD AND DEVICE FOR DETECTING CONTAMINANTS IN A FLUID

FIELD OF THE INVENTION

The invention relates to a method for detecting contaminants in a fluid and a device for carrying out the method.

BACKGROUND OF THE INVENTION

Fluids, especially lubricating oils or the like, are exposed to a continuous ingress of contaminants in the form of ferromagnetic particles, other metallic particles or other particles of contaminants in the operation of systems or devices. A certain maximum concentration of contaminants, depending on the application, can be tolerated for the operation of a system or of devices. Especially for rolling oils, as are used in the steel industry or heavy industry, under certain circumstances large amounts of contaminants are introduced. Their content can hardly be determined with sensors according to the prior art.

EP 290 397 B1 discloses a sensor for detecting the content of ferromagnetic particles in a fluid having a primary magnetic circuit formed by a permanent magnet. The primary magnetic circuit has an air gap which can be exposed to the fluid to cause the particles to collect in the vicinity of the air gap. The sensor also has a Hall element which detects the change of the magnetic flux depending on the collected contaminants. A proportional detector signal is achieved on the content of particles of contaminants in the fluid. A secondary magnetic circuit with an induction coil is designed to counteract the primary magnetic circuit of the permanent magnet up to a complete extinction of the magnetic field in the air gap. In this way, detachment of the particles collected in the air gap is enabled. The known sensors and measuring methods for determining the contamination of a fluid are, however, inherently unsuited to a substantial ingress of contaminants or ingress of metallic particles.

SUMMARY OF THE INVENTION

An object of the invention is to provide an improved device and method for operating the device in which very high concentrations of contaminants in a fluid can be determined.

This object is basically achieved with a method and with a device where before a contaminated fluid is routed to a sensor or a device for measuring the contamination, the contaminated fluid is diluted by adding a defined amount of cleaned, particle-free and contaminant-free fluid to such an extent that the particle density can be measured with the device. The degree of contamination in a fluid can then be determined with known measuring methods. The particle density or the degree of contamination of the undiluted fluid is computed by a control and/or regulation device or an arithmetic unit. The basic structure of the two fluids is preferably the same.

The contaminated fluid and the cleaned fluid can be mixed with one another in a mixer being a tank and/or a mixing valve.

In a device for carrying out the method, a metering circuit, that is, a hydraulic system, routes the contaminated fluid to the device for measuring the contaminants by a first pump or metering pump.

The metering pump is designed for transport of raw contaminated fluid, such as, for example, rolling oil, viewed in the fluid direction, and is located upstream of a first valve $V_1$ designed preferably as a 3/2 directional control valve. Depending on the operating position of this first valve $V_1$, contaminated fluid can travel either into the metering circuit to the tank or can be relayed in the direction of a connecting site of the main hydraulic system.

Furthermore, the device has a primary circuit comprising a second metering pump delivering contaminated and/or cleaned fluid to a sensor. A third valve $V_3$ and a fourth valve $V_4$ are designed to implement a cleaning mode or a mixing mode for cleaned and contaminated fluid together with the valves of the metering circuit. A measuring mode or an evacuation mode for the two circuits can be represented therewith.

A functional combination of metering circuit and primary circuit can be effected by the control and/or regulator such that the metering circuit remains in a preparation mode or standby mode, and such that the primary circuit is transferred into a cleaning mode for removing the contamination upstream of the sensor.

The method according to the invention for detecting contaminants in a fluid can be operated preferably in the following operating modes. To clean the oil located in the tank, the first valve $V_1$ is in its enabled position so that highly contaminated fluid in the form of the rolling oil is conveyed through, by the first metering pump, in the direction of the connecting site to the main hydraulic system. The first metering pump per unit of time continues to convey a large amount of fluid so that lines in the main hydraulic system can be flushed and deposits can be prevented. The rolling oil, within the scope of its current contamination, is thus conveyed back into the main hydraulic system.

The primary circuit, which has been decoupled for this purpose from the metering circuit relative to the valve $V_2$, has an enabling operating position so that the measuring device is bypassed. The valves $V_3$ and $V_4$ are switched such that in the closed circuit, fluid from the tank is conveyed through a filter adjoining the valve $V_4$ and is returned cleaned to the tank. In this way, the delivery rate of the other metering pump per unit of time is also high.

In the "measuring" operating mode, for purposes of checking the cleanliness of the mixed oil stored in the tank, the metering circuit, as described above, is decoupled again from the primary circuit. Also, the valve $V_2$, as a bypass valve, is kept in its blocked position to route the fluid through the measuring device. Furthermore, the valve $V_4$ is switched such that the cleaning filter is bypassed. In this measuring operation, the delivery rate of the second metering pump of the primary circuit is chosen to be small.

In the "mixing" and "metering" operating mode, the metering circuit leading to the mixing tank is in operation, i.e., the valve $V_1$ is switched such that contaminated fluid of the main hydraulic system travels into the tank.

The metered addition takes place either via a cycling of the valve $V_1$ or by corresponding reduction of the fluid delivery amount per unit of time through the first metering pump. The other metering pump of the primary circuit in turn has a high fluid delivery amount per unit of time. The measuring device in the form of the contamination sensor CS is again bypassed via the switched valve $V_2$. The valves $V_3$ and $V_4$ are switched such that the filter is again bypassed. Fluid is then returned directly from the valve $V_4$ into the tank.

This operating position relative to the primary circuit also corresponds to the "mixing" of the fluid in the primary circuit. The metering circuit then is decoupled from the tank by switching of the valve $V_1$. In turn, contaminated fluid continues to be delivered into the main hydraulic system with a high fluid delivery rate by the first metering pump. The latter operating position, with the metering pump decoupled from the primary circuit, also corresponds to the actual measuring process, that is, the measuring analysis to be carried out. The valve $V_2$ is blocked in the measuring process so that fluid is routed through the measuring device in the form of the contamination sensor by the other metering pump at low fluid delivery rate.

When a desired liquid level in the tank is exceeded, the device can be operated in an evacuation process in which tank fluid travels directly via the switched valve $V_2$ into the connection to the main hydraulic system, bypassing the measuring device by valve $V_3$. The valve $V_4$ then is in its blocked position. This evacuation can take place until the desired liquid level in the tank, which can correspond to a minimum liquid level in the tank, is in turn reached.

The sensor element can be a Hall element mounted at a collecting site intended for the quantity of contaminants, especially in the form of ferromagnetic particles. The sensor element determines the quantity of contaminants in the mixed fluid and transmits the output signal to a control and/or regulator. Advantageously a table of values can be stored in the control and/or regulator, which table establishes a relationship between the degree of dilution of the quantity of the contaminant. The output signal of the sensor element may also be highly nonlinear in this respect. The table of values can be based on empirically determined values. Alternatively, in the control and/or regulator, a function which has been determined, for example, by simulation can also be stored. That function represents the relationship between the amount of collected contaminant and the output signal of the sensor, depending on the degree of dilution of the fluid.

Depending on the measured values, the control and/or the regulator controls the metering circuit and the primary circuit in the combination of the above-described operating modes. In this connection, especially advantageously, when metallic/ferrometallic particles or contaminants are to be detected, a collecting site for collecting the contaminant of the fluid, in the form of a permanent magnet is provided in the device for measuring the contaminants. The magnet, is used to generate a magnetic field at the collecting site. A coil can be provided to move an element in the manner of an armature such that by moving the element, the magnetic field strength at the collecting site can be changed. Especially, the magnetic field strength can be reduced to such a degree that at least one part of the collected contaminant can be detached from the collecting site, in particular can be flushed out of the fluid of the metering circuit.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawings which form a part of this disclosure and which are schematic and not to scale.

DETAILED DESCRIPTION OF THE INVENTION

Figure 1:
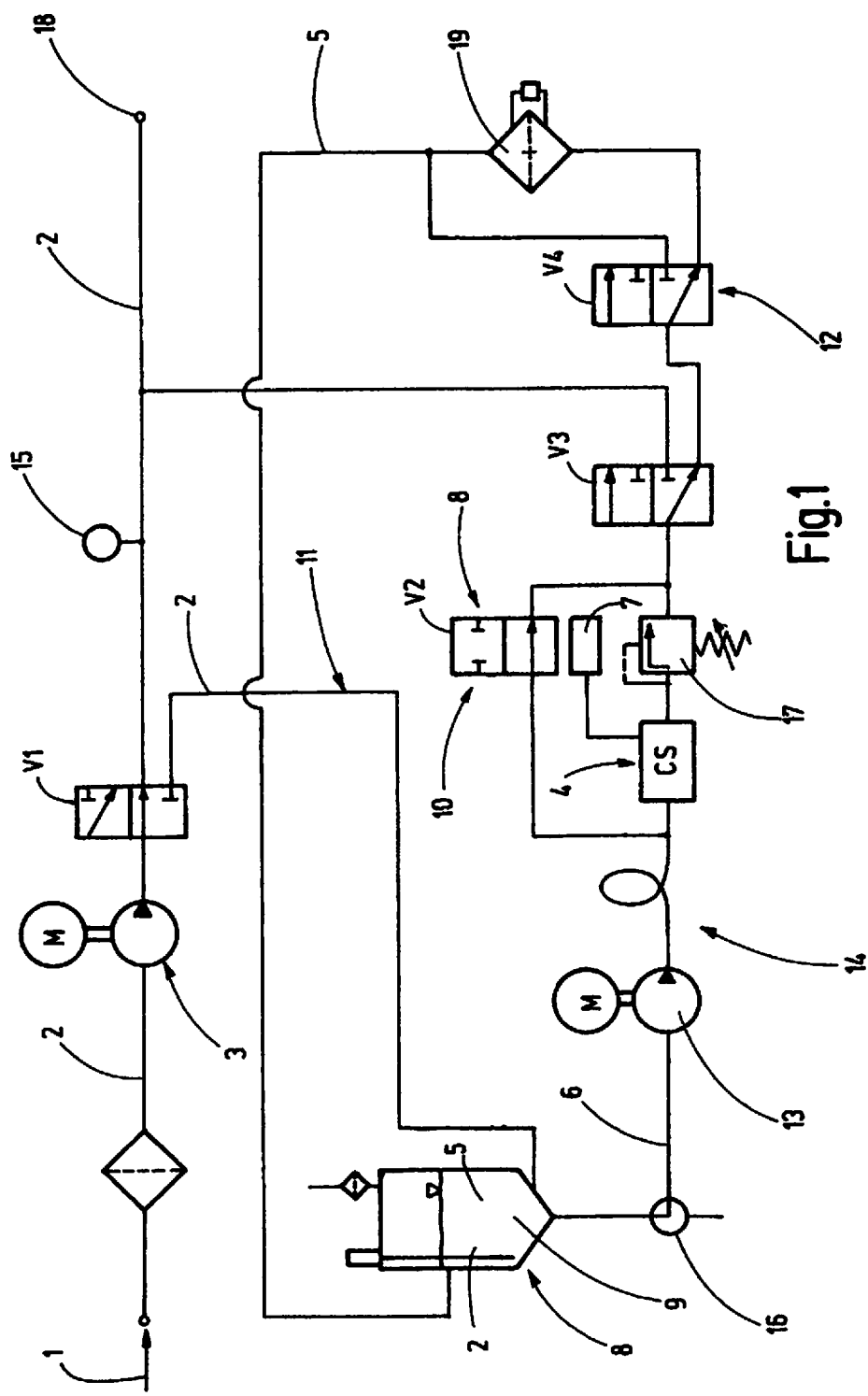
FIG. 1 is a hydraulic diagram in the manner of a function diagram of a device for carrying out a method for detecting contaminants according to an exemplary embodiment of the invention.

According to FIG. 1, a device 14 for carrying out a measuring method for detecting contaminants in a fluid 1 is shown in a schematic diagram. The fluid 1 in the illustrated exemplary embodiment is a rolling oil of a mill train or rolling system (not detailed) which is correspondingly highly contaminated and which has a very high content of metallic, especially ferromagnetic particles, in addition to other contaminants, such as slag.

The device 14 includes essentially a metering circuit 11 and a primary circuit 12.

The metering circuit 11 has a first metering pump 3 with a stepping motor drive. The first metering pump 3 conveys contaminated fluid 2 with particles. The first valve $V_1$ is designed as a 3/2 directional control valve and is shown in its enabled position in FIG. 1 in which the contaminated fluid 2, routed via a shavings sensor 15, is routed to a connection 18 of a main hydraulic system. Fluid is supplied in return flow to the mill train. The shavings sensor 15 is optional and is not critically necessary for the actual function of the measuring and dilution system, which is still to be detailed. A third valve $V_3$ is likewise designed as a 3/2 directional control valve, like the first valve $V_1$. The third valve $V_3$, in its operating position shown in FIG. 1, is in a passage position to a fourth valve $V_4$. The first valve $V_1$, in its other operating position, enables the delivery of contaminated fluid 2 to a tank 9, which tank is part of a mixer 8. Mixer 8 also includes a second valve $V_2$ that is not critically necessary for the basic function of the device.

The primary circuit 12 essentially comprises the tank 8, an evacuation site 16 for the metering circuit 11, a second metering pump 13, as well as a device 4 for measuring the contamination of the fluid 1. The device 4 can be supplied with a defined mixture of cleaned fluid 5 from the tank 8 and contaminated fluid 2, that is, a type of mixed fluid 6.

The device 4 for measuring the contamination of the fluid 1 can be a contamination sensor CS, as is described, for example, in DE 10 2006 005 956.5. These contamination sensors CS work in the manner of light-based particle sensors, i.e., the particles—after passing through a photoelectric barrier or the like—are determined according to size and number so that the dilution aspect of the measuring fluid, which will be detailed below, acquires increased importance. Only by the indicated dilution or deconcentration of the fluid medium according to the invention within the definable, adjustable framework are the particles to be detected present individually in a statistical distribution in the fluid such that the light-based sensors can respond at all. Without this separation by dilution, only a fluid clouded by the particles could be established without any indication about how the degree of contamination is in fact represented in particular, due to the lack of counting magnitude relative to the general particle contamination. The dilution to be carried out is oriented predominantly to the measuring quality of the respective light sensor to be used.

A pressure control valve 17 located downstream of the device 4 for measuring the contaminants provides for bubble-free, preloaded operation of the device 4. Between the second metering pump 13 and the contamination sensor CS, an inlet segment for the fluid, whose length can be defined at will, is represented in the form of a loop. The second valve $V_2$, designed as 2/2 directional control valve, is used as a bypass valve or mixing valve 10. In this respect, the second valve $V_2$ enables the device 4 and the pressure control valve 17 to be bypassed. In conjunction with the operating position of the third valve $V_3$ and of the fourth valve $V_4$, likewise designed as 3/2 directional control valves, the position shown in FIG. 1 permits a backflow of mixed fluid 6 into the tank 8. Depending on the operating position of the fourth valve $V_4$, flow through an additional filter 19 can take place or not. However, in the circuit diagram as shown in FIG. 1, fluid flow through the filter 19. The second valve $V_2$ is not absolutely necessary. When second valve $V_2$ is omitted, in each case, fluid flows through the contamination sensor CS and the pressure control valve 17.

The first, third, and fourth valves $V_1$, $V_3$, and $V_4$ are designed as 3/2 directional control valves so that the valve modules used in this respect are designed as identical components. This design helps reduce the hardware cost so that the entire device can be economically produced. All valves can preferably be electromagnetically actuated that is not detailed for the sake of simplicity.

An arithmetic unit 7, which can be part of a control and/or regulator (not detailed) or can be part of the device 4 for measuring the contamination in the fluid, computes the content of particles of contaminants determined by the device 4 back to the actual content of particles of contaminants in the unmixed fluid 2. The particle contamination is from the main hydraulic system which, in this example, transports the rolling oil of the mill train. Instead of the indicated rolling oil, any other form of more or less heavily contaminated fluid with ingress of particles can also be treated via the described method and device.

Figure 2:
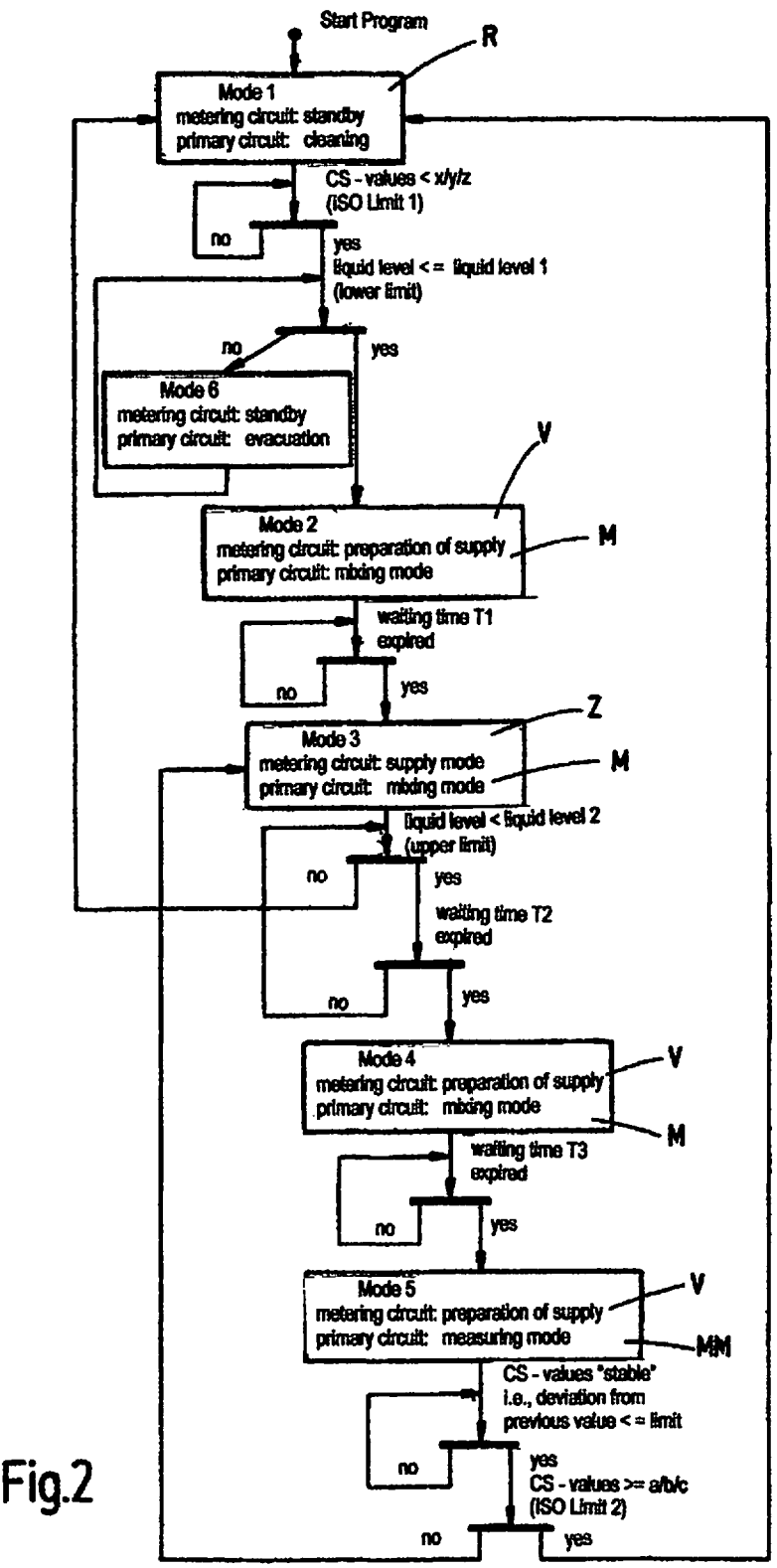
FIG. 2 is a flow chart of a method for detecting contaminants in a fluid by the device as shown in FIG. 1.

FIG. 2 depicts, in the form of a flow chart, one of many operating modes or methods for detecting contaminants with the device 14 shown in FIG. 1. Within the scope of a first operating mode (mode 1), the metering circuit 11 is in a standby mode, and the primary circuit 12 is in a cleaning mode R.

Figure 3:
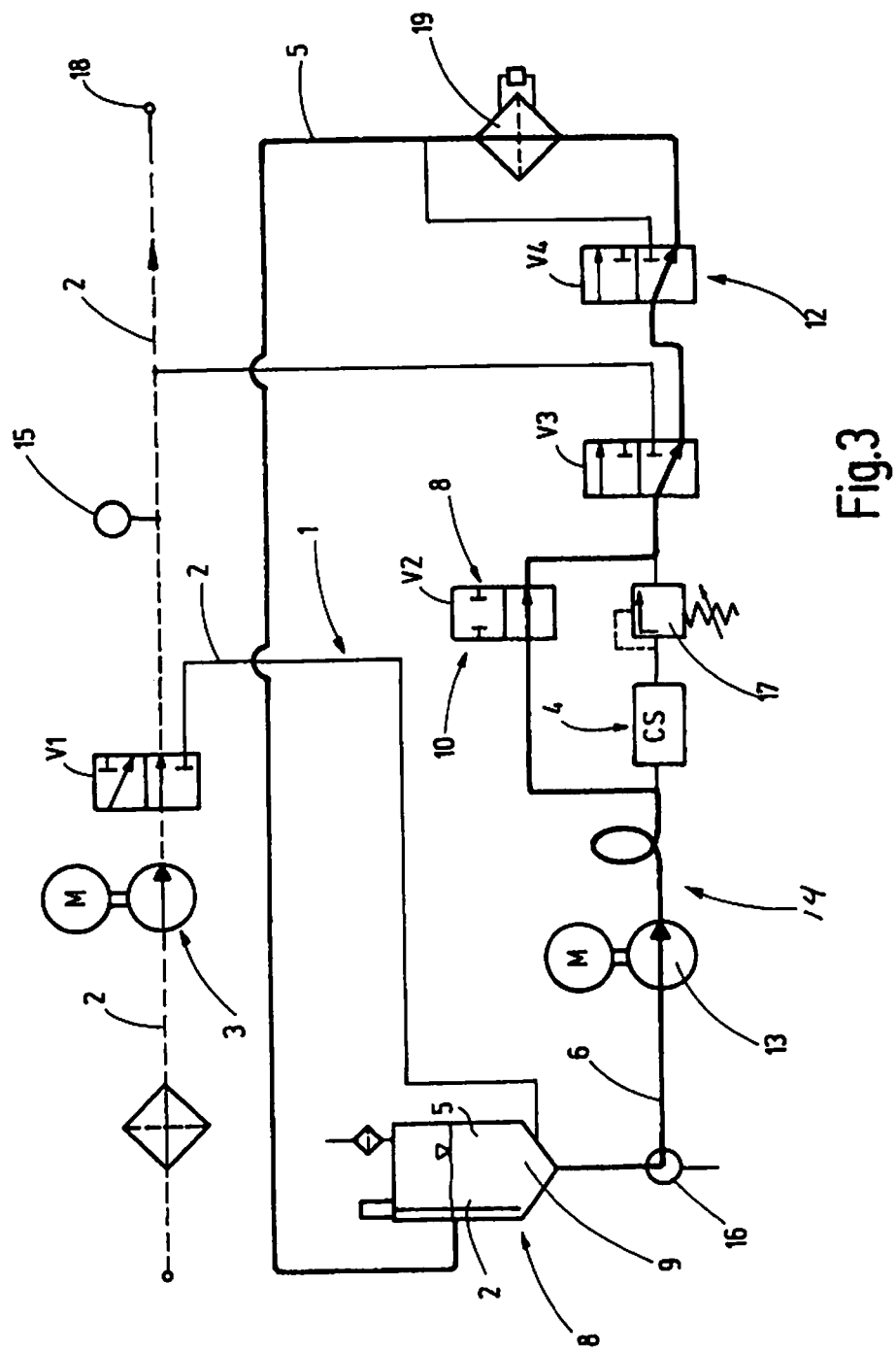
FIGS. 3 to 5 are hydraulic diagrams of the device of FIG. 1 in different operating modes.

Another operating situation, "cleaning of the oil," is illustrated in FIG. 3. In the line part shown with the broken line, preferably a large amount of fluid is moved through the working circuit by the stepping motor drive and the metering pump 3 in order to flush, for example, the connected lines. This operation helps prevent deposits. Fluid with current contamination continues to be supplied via the connection 18 to the main hydraulic system from the input side. The first valve $V_1$ is in its illustrated enabled position.

The primary circuit 12 (shown by a bolded line) is supplied with cleaned fluid routed via the filter 19. Here the second valve $V_2$, and the third and fourth valve $V_3$, $V_4$ are in respective illustrated operating positions such that the fluid flow produced by the second metering pump 13 is routed past the sensor CS or the device 4 by the third valve $V_3$ and fourth valve $V_4$ and can be returned in this respect to the tank 9 in a closed circulation. This circulation repeats until a defined degree of purity for the fluid 5 is reached. In this process of cleaning the oil via the filter 19, the stepping motor drive is operating with the second metering pump 13 in the range of large amounts of fluid per unit of time in the primary circuit 12.

In the pure mixing operation for mixing of cleaned fluid 5 with contaminated fluid 2, the valve $V_4$ is switched such that the filter 19 is then bypassed. Changing into a mode 2 or a mixing mode M in which cleaned fluid 5 is mixed in a defined manner with contaminated fluid 2 is possible. This mode largely corresponds to FIG. 4 which shows a "mixing and metering process." The metering circuit 11 (shown by broken lines) shifts into a prepared supply mode V in which contaminated fluid 2 is supplied to the mixer 8, here in the form of the tank 9. For an especially favorable progression of the method, the connecting line between the tank 9 and the valve $V_1$ should be dimensioned to be especially short, for example, chosen to have a line length of less than 10 cm. For this charging or admixing process, the metering pump 3 delivers only a small amount of contaminated fluid 2 per unit of time. Instead of low charging via the pump 3, the valve $V_1$ can also shift into correspondingly cycled operation in which a certain portion amount from the main line with the rolling oil is always taken into the metering circuit 11 in a stepwise fashion. In this case, the arithmetic unit 7 takes over the cycled operation for the valve $V_1$.

Figure 4:
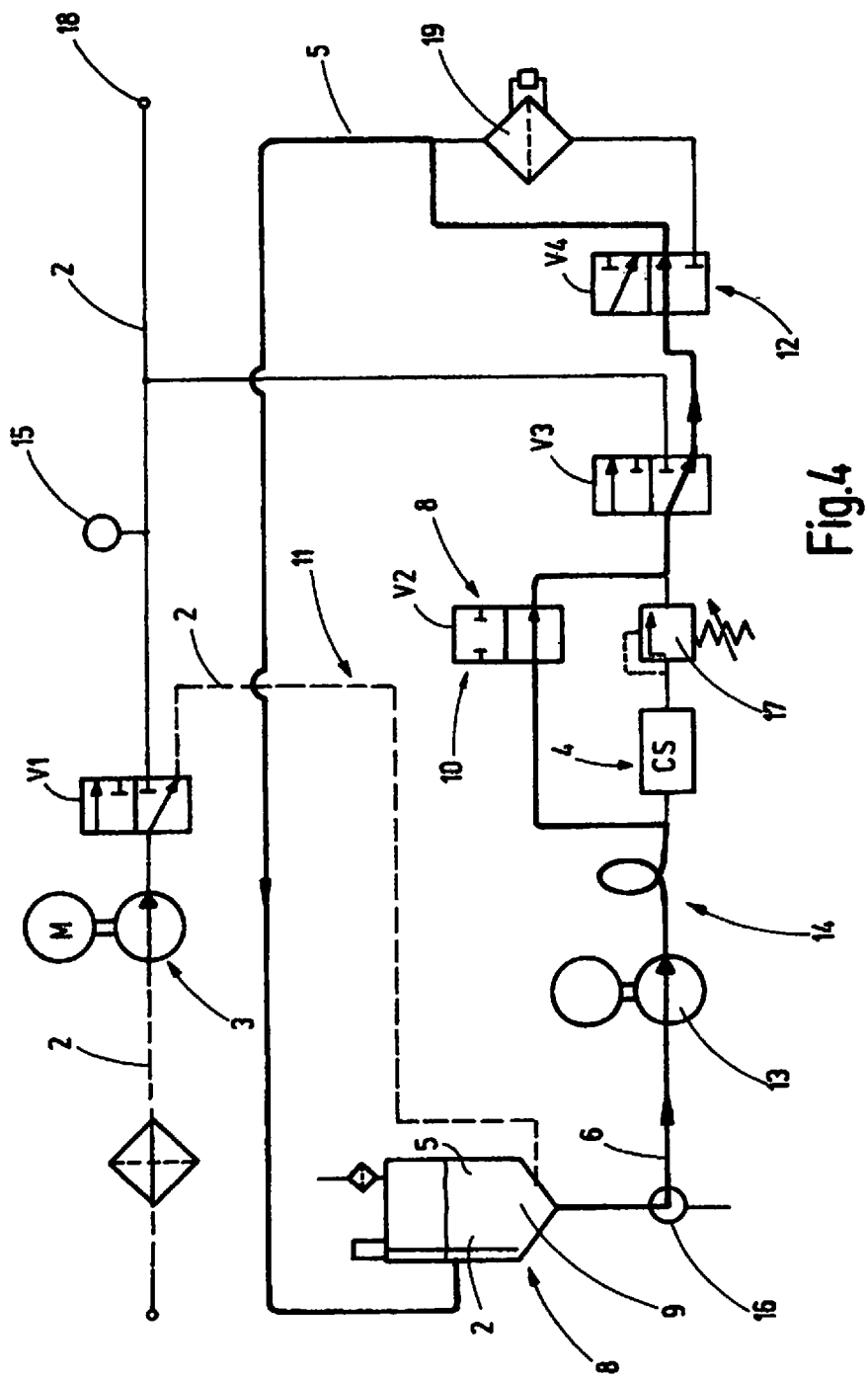

The third valve $V_3$ and the fourth valve $V_4$ are in an illustrated operating position shown in FIG. 4. The filter 19 is bypassed into this mode so that fluid from the second metering pump 13 in turn is routed to the mixer 8 at a high flow amount per unit of time.

After a definable waiting or resting time, a change is made to mode 3 in which the metering circuit 11 is in a supply mode Z for contaminated fluid 2 to the mixer 8, and the primary circuit 12 (in turn shown by the bolded line) remains in a mixing mode M. The operating position of the first valve $V_1$ here is such that contaminated fluid 2 is conveyed into the mixer 8. The operating position of the second valve $V_2$, and of the third and fourth valve $V_3$, $V_4$, as shown in FIG. 4, is such that mixed fluid 6 is moved past or bypasses the device 4 for measuring the contaminants to the mixer 8 in the closed circuit.

Depending on the desired purity level, the mixing ratios between contaminated fluid 2 and cleaned fluid 5 are set preferably between 1:10 to approximately 1:150. For example, one milliliter of contaminated fluid 2 is mixed with 10 milliliters of cleaned fluid 5. A definable amount of cleaned fluid 5 has to already be in the tank 9 prior to this admixture process of contaminated fluid via the metering circuit 11. The liquid level in the tank 9 in the figures relates to the minimum liquid level of the tank 9.

Figure 5:
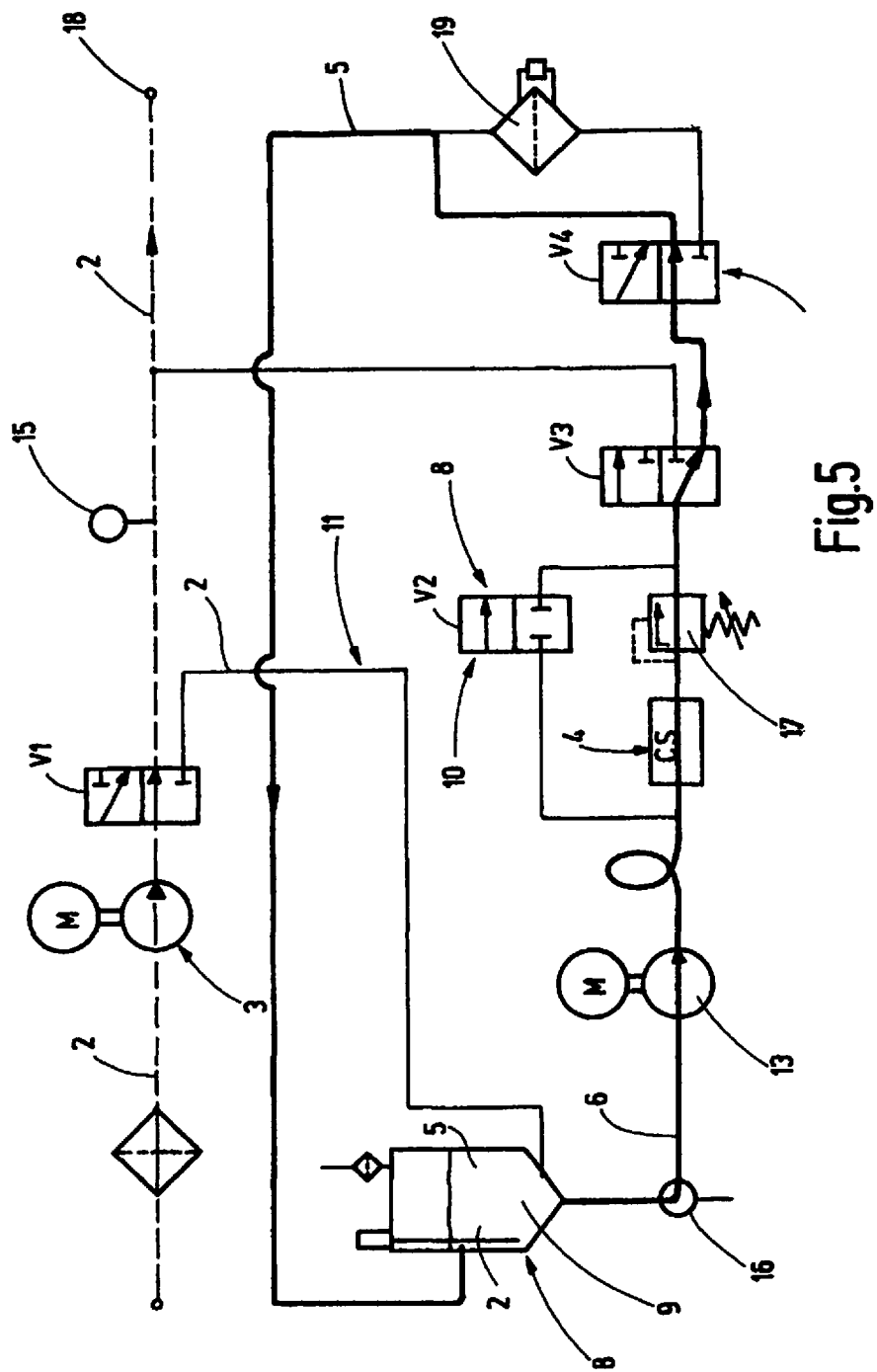

After a definable waiting time expires again, the method in the primary circuit 12 (in turn shown by a bolded line) shifts into a measuring mode MM (mode 5). In this measuring operation, which corresponds to the operating representation shown in FIG. 5, the metering circuit 11 is in an operating mode in which contaminated fluid is routed directly from the input side to the main hydraulic system via the connection 18, comparably to the representation in FIG. 2. This primary circuit runs as shown in turn by the broken line. The second valve $V_2$ is in its illustrated blocking position. The fourth valve $V_4$ and the third valve $V_3$ are in their illustrated operating position in which mixed fluid 6 is routed through the device 4 for measuring the contaminant. The filter 19 remaining omitted. In turn, per unit of time the metering pump 3 delivers a large amount of fluid, and the metering pump 13 delivers a small amount. The required measurement values are determined individually as soon as their variance does not exceed a certain boundary.

As FIG. 2 shows, another operating mode (mode 4) is switched between mode 5 and mode 3, in which the metering circuit 11 is shifted into preparation of supply V, and the primary circuit 12 is switched into the mixing mode M. In mode 6, the metering circuit 11 is in the standby mode. In a further provided evacuation, a desired liquid level in the tank 9 is attempted. In an enabled operating position of the valve $V_3$, the amount of fluid of the primary circuit 12 is returned as return flow into the main hydraulic system via the connection 18. Then there can again be a change to mode 1 as the operating mode.

In a simplified embodiment (not shown) of the method according to the invention in addition to the device, the tank 9—in addition to the evacuation site 16—can also be omitted. The valve $V_1$ on the output side is switched directly to the input side of the second metering pump 13 via the metering circuit 11. In this case, the connecting line between the valve $V_1$ and the metering pump 13 in turn is chosen to be short. Likewise a short connection is sought between the output of the second metering pump 13 and the input of the contamination sensor CS. In the correspondingly simplified embodiment, the bypass valve or mixing valve $V_2$ can also be omitted, as well as the pressure control valve 17. As already stated, the shavings sensor 15 can also be omitted. The required admixing takes place, as already stated, via connection of the metering pump 3 and preferably by cycled operation of the valve $V_1$, which can then transfer contaminated fluid 2 in batches into the metering circuit 11.

In a further simplified embodiment (not shown), the contaminated fluid with the particle contamination, such as, for example, rolling oil, is routed quantitatively controlled directly via the metering pump 3 to the input of the second metering pump 13. Second metering pump 13 on its output side then has the device 4 for measuring the contaminants. In a branch upstream of the second metering pump 13, it can convey fresh oil from a supply source, such as, for example, a barrel. This extremely simple solution manages without any valve control and therefore without valves which must be actuated. In turn, the fluid which has been measured in this way via the contamination sensor CS is then returned to the main hydraulic system, for example in the form of the mill train.

Instead of the tank 9 or the indicated branch between the metering pumps 3 and 13, a mixing valve could be provided, which mixing valve is not defined in detail and in turn undertakes admixing actuated via the arithmetic unit 7. Furthermore, for an embodiment of the measuring and admixing device, which is not detailed, the metering circuit 11, with a supply line coming directly from the valve $V_1$, can be switched upstream of the contamination sensor CS. This embodiment aids integration of the device into all possible valve blocks. The supply line therefore ends downstream of the other metering pump 13 in the fluid segment to the sensor CS.

While one embodiment has been chosen to illustrate the invention, it will be understood by those skilled in the art that various changes and modifications can be made therein without departing from the scope of the invention as defined in the appended claims.

What is claimed is:

1. A particle detection method for detecting contaminants in a fluid, comprising the steps of:
    conveying contaminated fluid with a first metering pump to a device for measuring at least one of fluid contamination and particle density in a contaminated fluid;
    before the contaminated fluid enters the device, mixing the contaminated fluid with cleaned fluid, obtained by removing particle contamination from the contaminated fluid, in a defined mix ratio to produce a mixed fluid;
    measuring at least one of fluid contamination and particle density in mixed fluid; and
    determining at least one of fluid contamination and particle density of the contaminated fluid by an arithmetic unit.

2. A particle detection method according to claim 1 wherein the contaminated fluid and the cleaned fluid are mixed in a mixer.

3. A particle detection method according to claim 2 wherein the mixer comprises at least one of a tank and a mixing valve.

4. A particle detection method according to claim 1 wherein
    the contaminated fluid is conveyed by the first metering pump in a metering circuit in a supply mode to a mixer; and
    the contaminated fluid is mixed with the cleaned fluid in a primary circuit.

5. A particle detection method according to claim 4 wherein
    the primary circuit is a measuring mode in which the mixed fluid flows through a contaminant sensor and bypasses a fluid cleaner that produced the cleaned fluid to convey fluid in the primary circuit back to the mixer, while the metering circuit is in a preparation mode supplying the contaminated fluid to a contaminated fluid outlet for supplying a hydraulic system.

6. A particle detection method according to claim 4 wherein
    the contaminated fluid in the metering circuit is not moved while at least one of the cleaned fluid and the mixed fluid is evacuated from the mixer into the primary circuit.

7. A particle detection device for detecting contaminants in a fluid, comprising:
    a metering circuit including a contaminated fluid inlet, including a first metering pump downstream of and in fluid communication with said contamination fluid inlet, including a first valve downstream of and in fluid communication with said first metering pump and including a contaminated fluid outlet downstream of said first valve and in selective fluid communication with said first metering pump in a first position of said first valve;
    a mixer downstream of said first valve and in selective fluid communication with said first metering pump in a second position of said first valve;
    a contaminant sensor downstream of and in fluid communication with said mixer to measure at least one fluid contamination and particle density of fluid passing therethrough;
    a fluid cleaner downstream of said first valve and in selective fluid communication with said first metering pump in one position of said first valve, said fluid cleaner including a filter producing cleaned fluid from the contaminated fluid by removal of particle contamination, said mixer being in fluid communication with said fluid cleaner to mix the contaminated fluid with the cleaned fluid in a defined ratio to form a mixed fluid upstream of said contaminant sensor such that said contaminant sensor can measure the mixed fluid; and
    an arithmetic unit coupled to said contaminant sensor to determine at least one of particle density and contamination of contaminated fluid.

8. A particle detection device according to claim 7 wherein
    a primary circuit comprises a second metering pump in fluid communication between said mixer and said contaminant sensor, comprises a third valve in fluid communication between said contaminant sensor, said fluid cleaner and said contaminated fluid outlet, and comprises a fourth valve in a bypass line around said fluid cleaner and being downstream of and in fluid communication with said third valve.

9. A particle detecting device according to claim 8 wherein said first, third and fourth valves operate said metering circuit in a standby mode while said primary circuit is operated in a cleaning mode.

10. A particle detection device according to claim 9, wherein
    a second valve is located in a bypass line around said contaminant sensor;
    said mixer comprises a tank; and
    while said first valve connects said first metering pump to said contaminated fluid outlet in fluid communication, said second, third and fourth valves connect said tank to a second metering pump, connect said second metering pump via said second valve to said third valve without passing through said contaminant sensor and connect said fourth valve to said tank via said filter in fluid communication.

11. A particle detection device according to claim 10 wherein
said valves operate in preparation and mixing modes supplying contaminated fluid to said mixer with cleaned fluid.

12. A particle detection device according to claim 11 wherein
said valves operate in the preparation and mixing modes to connect said second metering pump to said mixer while said second valve opens said bypass line such that fluid does not flow through said contaminant sensor.

13. A particle detection device according to claim 8 wherein
a second valve is located in a bypass line around said contaminant sensor; and
in a mixing mode, said first valve connects said first metering pump to said mixer to convey contaminated fluid to said mixer, and said second, third and fourth valves convey a mixed fluid of contaminated fluid and cleaned fluid to bypass said contaminant sensor and to return to said mixer.

14. A particle detection device according to claim 8 wherein
a second valve device is located in a bypass line around said contaminant sensor; and
in a measuring mode, said first meter pump is operated with said first valve conveying contaminated fluid to said contaminated fluid outlet, and said second valve is in a blocking positing conveying a mixed fluid of contaminated fluid and cleaned fluid to said contaminant sensor for measurement and then to said tank via the third valve with the fourth valve bypassing said fluid cleaner.

15. A particle detection device according to claim 8 wherein
a second valve is located in a bypass line around said contaminant sensor; and
in an evacuation mode, said second valve opens to convey contaminated fluid to said third valve bypassing said contaminant sensor, said third valve is open to contaminated fluid outlet, and said fourth valve is in a blocking position bypassing said fluid cleaner.

16. A particle detection device according to claim 7 wherein
said contaminant sensor comprises at least one of an optical sensor and a Hall sensor, and is coupled to a control connected to and controlling operation of said valves and said metering pumps.

* * * * *